United States Patent [19]

Chan et al.

[11] Patent Number: 5,464,623
[45] Date of Patent: Nov. 7, 1995

[54] PROCESS FOR PELLETIZING INSECTICIDAL N-HYDROCARBOYL PHOSPHOROAMIDOTHIOATES AND PHOSPHOROAMIDODITHIOATES

[75] Inventors: Jimmy H. Chan, Martinez; Rodrick I. Satre, Point Richmond; James H. Trusler, Pleasant Hill; Sadanand G. Memula, Fremont, all of Calif.

[73] Assignee: Chevron Research Company, San Francisco, Calif.

[21] Appl. No.: 395,969

[22] Filed: Aug. 18, 1989

[51] Int. Cl.⁶ .......................... A01N 25/00; A01N 57/00
[52] U.S. Cl. .......................... 424/405; 514/120; 514/951
[58] Field of Search ..................... 514/118, 119, 514/120, 951; 558/178; 624/450

[56] References Cited

U.S. PATENT DOCUMENTS

| | | | |
|---|---|---|---|
| 3,716,600 | 2/1973 | Magee | 558/178 |
| 3,845,172 | 10/1974 | Magee | 558/178 |
| 3,914,417 | 10/1975 | Magee | 514/120 |

*Primary Examiner*—Marianne M. Cintins
*Assistant Examiner*—K. Weddington
*Attorney, Agent, or Firm*—Fish & Richardson

[57] ABSTRACT

Insecticidal pellet compositions of N-hydrocarboyl phosphoroamidothioates and phosphoroamidodithioates are provided. These compositions have improved odor control, thermal stability, attrition resistance, bulk density and handling characteristics over the powdered forms of the insecticides. Methods are provided for making such pellets, and in particular, an extrusion method is provided in which the dry insecticidal composition is mixed with from 3-25% of a solvent to form a consistency of damp sandy loam and then extruded.

39 Claims, No Drawings

PROCESS FOR PELLETIZING INSECTICIDAL N-HYDROCARBOYL PHOSPHOROAMIDOTHIOATES AND PHOSPHOROAMIDODITHIOATES

The present invention is directed to pelletized insecticidal compositions and methods of making the same. In particular the present invention is directed to making pelletized insecticidal N-hydrocarboyl phosphoroamidothioates and phosphoroamidodithioates.

BACKGROUND OF THE INVENTION

Certain N-hydrocarboyl phosphoroamidothioates and phosphoroamidodithioates .have high insecticidal activity. A particularly important commercial insecticide within these classes of compounds is the insecticide ORTHENE®, which can be systemically taken up by a plant so that insects which feed and/or live on the plant are killed, in addition to those insects which directly ingest or are contacted by the insecticide. See U.S. Pat. Nos. 3,716,600, 3,845,172 and 3,914,417. ORTHENE® is commercially produced as technical grade chemical of about 97 to 99.5% purity. One method of formulating technical grade ORTHENE® for commercial use is to mix the technical grade powder with an anti-caking agent, such as fumed silica, and a wetting agent. The wetting agent is utilized to wet the ORTHENE® and the anti-caking agent is used to prevent agglomeration of the ORTHENE® in its container.

The wetting agent is utilized to improve the spread-out of ORTHENE® when it is applied to crops as a spray solution, or when applied as a dust, after exposure to moisture via rain, dew, or irrigation. The powdered commercial forms of ORTHENE® are available in dilutions referred to as ORTHENE® 90S, ORTHENE® 75S, ORTHENE® 50S, and in other commercial dilutions.

The powder form allows formulations of ORTHENE® to relatively high concentrations, e.g., ORTHENE® 90S. Other, lower concentrate formulations are targeted to discrete markets using a soluble powder signified as -xxS. In most cases, the application of ORTHENE® xxS to the crop is via a water solution spray. The anti-caking agents, while promoting product flowability during the solution/mixing process, do not enhance the solution method of application. On the other hand, inherent to all powders, handling difficulties due to dust make this form of product less desirable than liquids and agglomerate forms. Furthermore, ORTHENE® has a characteristically objectionable odor (believed to be organothio compounds) which is compounded by the problems with dust.

ORTHENE® is available in liquid form, which minimizes or eliminates airborne contamination due to dust. However, due to storage stability limitations of solutions, its concentration is limited to a maximum of 25%, the balance being solvent and adjuvants. ORTHENE® in a liquid formulation has a solvent and packaging expense as well as a container disposal requirement that makes it less attractive to the consumer on the basis of price and empty container disposal requirements.

An agglomerate form of ORTHENE® which also minimizes airborne contamination due to dust, has been constrained to dilute concentrations of ORTHENE® applied to large particles by spraying and then dried, or as a dilute concentration of ORTHENE® combined with binders and anti-caking agents to form agglomerates via processes known to those skilled in the art, such as, pan granulation, extrusion, fluid granulation, pelletizing. The concentration of ORTHENE® via these methods has heretofore been limited to a concentration no greater than about 36% to 50%, with known commercial products typically no more than 5% ORTHENE. The limit on concentration of ORTHENE® was due to the melt property of ORTHENE® limiting the feasible operability of this form of product. Concentration of active ingredient is further limited by the ability of binding agents to form agglomerates, i.e. a minimum amount of any particular binding agent is required in order to meet physical properties of attrition resistance, crush strength and bulk density. In the case where liquid ORTHENE® solutions were sprayed on agglomerates and then dried, the limitation of concentration was due to the practical wetting ability of the receiving agglomerate. Too much liquid applied would form a mud. At these low levels of ORTHENE® concentration, commercial products require more handling and are less attractive formulations for applications of ORTHENE® made via solution spraying.

The ORTHENE® xxS formulations have problems due to the anti-caking agent ingredients. Anti-caking agents are not soluble in water (the typical application spray solvent) or other normal solvents. Due to their insolubility, they can settle in the applicator's spray tank. The settled anti-caking agents plug spray nozzles which detracts from the marketability of the ORTHENE® xxS product line. This spray nozzle plugging problem can occur when ORTHENE® xxS products are tank mixed with other commercial pesticides, which is a normal farming industry practice. While methods to minimize the occurrence of anti-caking agent settling have evolved, they require special procedures to avoid nozzle plugging conditions, which adds to the inconvenience of using ORTHENE® xxS.

Furthermore, anti-caking agent segregates in the manufacturing process equipment during material handling procedures and forms insoluble bits of anti-caking agent which can cause nozzle plugging.

Therefore, alternative forms to ORTHENE® powders, that resolve problems characteristic of dusts are desired by both the manufacturer and the marketplace. One possible alternative to a powdered ORTHENE® is in the form of a pellet: a cylindrically shaped solid. Pellets practically eliminate the dust problems and reduce the surface area-to-weight ratio which mitigates the odor problem.

However, currently available ORTHENE® pellets, as mentioned above, contain relatively small amounts of ORTHENE® typically no more than 5% active ingredient. Attempts to manufacture technical assay (approximately 97% active ingredient) ORTHENE® pellets from the dry ORTHENE® technical powder have been unsuccessful. The anti-caking agents and binders needed to make the currently available ORTHENE® pellets add to product cost, can cause excess wear and tear on equipment, and by dint of being a major fraction of the product formula, require more bulk product than the concentrated powders in order to deliver effective amounts of ORTHENE® to the protected crop.

Additionally, the anti-caking agents and binders used to form the currently available ORTHENE® pellets have the same water insolubility problem that the anti-caking agent has in ORTHENE® powdered formulae. Because of that, commercial ORTHENE® pellet products are limited to use by direct application to the crop; i.e., placing individual pellets on or around each plant, which is impractical for most commercial farming ventures.

It is thus an object of the present invention to provide pelletized forms of insecticidal N-hydrocarboyl phosphoroamidothioates and phosphoroamidodithioates containing high concentrations of insecticidal active ingredient.

It is a further object of the present invention to provide methods for making such pelletized compositions.

These and other objects of the invention will be apparent from the following description and from the practice of the invention.

SUMMARY OF THE INVENTION

The present invention provides insecticidal compositions comprising pellets which contain as active insecticidal ingredients, a compound or mixture of compounds of the formula:

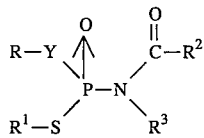

wherein R and $R^1$ individually are alkyl, alkenyl or alkynyl of up to 6 carbon atoms, $R^3$ is hydrogen or alkyl of 1–6 carbon atoms, $R^2$ is hydrogen, alkyl of 1–18 carbon atoms, cycloalkyl of 3–8 carbon atoms, alkenyl of 2–18 carbon atoms or alkynyl of 3–18 carbon atoms, and Y is oxygen or sulfur; and the pellets are characterized by an attrition resistance of at least about 92%, a mean hardness of greater than about 1.5 lb-F and a bulk density of at least about 42 lb/ft$^3$ (about 0.68 gm/cc). Methods are also provided for making such solid pellets by extrusion or molding of a pourable or moldable composition of the insecticide with a solvent, or of a hot melt of the insecticide. The concentration of ORTHENE® in these pellets is in the range of about 75% to 97% a.i., with the most likely concentration of 97% a.i.

DESCRIPTION OF THE PREFERRED EMBODIMENTS

The pellets according to the present invention are characterized by an attrition resistance of at least about 92%, a mean hardness of greater than about 1.5 lb-F and a bulk density of at least about 42 lb/ft$^3$ and may be made to any convenient size. Useful pellets will be extrudates of about 3 mm to 25 mm in length with diameters from about 1.5 mm to 7 mm. Spherical pellets are also useful having diameters of about 1 mm to 5 mm. The active insecticidal ingredient of the pellets will be a compound or a mixture of compounds of the formula:

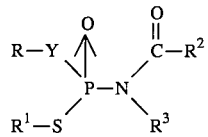

wherein R, $R^1$, $R^2$, $R^3$ and Y are as described hereinabove. Particularly preferred compounds are those in which R and $R^1$ are independently methyl, ethyl, allyl or alkenyl; $R^2$ is H or alkyl; and $R^3$ is hydrogen; and Y is oxygen. The most preferred compound is that in which R, $R^1$ and $R^2$ are methyl, $R^3$ is hydrogen and Y is oxygen. Compounds of the above formula may be prepared as described in technical form in U.S. Pat. Nos. 3,716,600, 3,845,600 and 3,914,417 which usually provide compositions of about 97–98.5% purity. This technical grade insecticide may optionally be admixed with one or more additives prior to being pelletized as described hereinafter.

One additive may be ammonium sulfate, in an amount less than about 5% by weight of the total pellet composition, preferably 2% or less by weight of the total pellet composition. This small amount of ammonium sulfate imparts a slight acidity to the pellet composition which is desirable for stability.

Another additive may be anhydrous magnesium sulfate, in amount up to about 5% by weight of the total pellet composition, preferably 2% or less by weight. This serves as a dehydrating agent will absorb trace amounts of water present in the pellets to prevent hydrolysis of the insecticide.

Various surfactants may also be utilized, usually less than 20% by weight of the total composition, which would assist in dispersion of the insecticide on the crops. Potential surfactants include various polymeric surfactants which are known by the trade name "Pluronic®" series and "Tetronic®" series sold by BASF.

Small amounts of deodorants may also be used as additives.

Another additive may comprise a small amount of an anti-caking agent, i.e. less than about 1% by weight, and usually at least about 0.1% by weight of the total dry pellet composition. While an anti-caking agent is not necessary, it is preferred, particularly for prolonged storage of the pellets since the pellets may lightly cohere when exposed to high humidity, temperature or pressure. The preferred anti-caking agent is a fumed silica under the trade name Wessalon S applied as a coating to pellets.

In the most preferred embodiment according to the present invention the pellets are made by making a pourable or extrudable mixture of the solid technical insecticide composition with a solvent, optionally containing the dry additives. The solvent should be selected such that the insecticidal composition has a solubility in that solvent at 20° C. of at least about 0.5 gm/100 ml. Preferably the solvent should also have a relatively high volatility at atmospheric pressure so that the pellets may be dried (i.e., freed of solvent) without or with only minimal application of heat. Hence, exemplary solvents are (ranging from that in which the insecticide is least soluble to that in which the insecticide is most soluble) are hexane, carbon tetrachloride, toluene, isopropanol, ethanol, chloroform, methanol, methylene chloride and water. The most preferred solvent is methylene chloride. Table 1 shows properties typical to pellets made using different solvents.

TABLE 1

ORTHENE ® PELLETS - ATTRITION RESISTANCE/ CRUSH STRENGTH

ORTHENE ® pellets were made with various solvents.
Attrition resistance: ASTM method D-4058-87. 1 kg
ORTHENE ® pellets were placed in a bagged sample on a
vibrating transportation simulator for 1 hour at 1.0
G force. The attrition is tested by sieve analysis.
Crush Strength: ASTM method D-3313-88. Crush
strength is measured with a Chatillon DPP 10 gauge on
a representative pellet sample.

| Solvent | % Attrition Resistance | Crush Strength Lb-force |
|---|---|---|
| Methylene Chloride + AS + Wessalon S | 99.9 | 2.34 |
| Methanol | 99.7 | 1.67 |

TABLE 1-continued

ORTHENE ® PELLETS - ATTRITION RESISTANCE/
CRUSH STRENGTH

| Ethanol | 99.4 | 1.81 |
| --- | --- | --- |
| Methylene chloride | 99.0 | 2.60 |
| Isopropanol | 97.8 | 0.90 |
| Water | 97.4 | 2.48 |
| Chloroform | 94.1 | 1.67 |
| Methylene chloride + Pluronic 3 wt % | 92.0 | 2.58 |
| Toluene | 89.2 | 1.15 |
| Carbon Tetrachloride | 88.9 | 0.93 |
| Dichloroethane | 87.2 | 1.63 |

According to the preferred method of making pellets of the present invention, the dry ingredients (comprising the insecticide and additives, if present) are mixed with the solvent, preferably methylene chloride, in amount of about 3–25% by weight of solvent. The proper amount of solvent will form an extrudable mixture having the consistency of damp sandy loam (as is used in the field of materials science) and form dry pellets having the properties given above within the scope of the invention. The amount of solvent required to form the proper consistency and to yield the desired pellet properties is inversely relative to the solubility of the insecticide in the solvent, i.e., the more soluble the insecticide the less solvent is needed to attain the desired consistency. Although a damp sandy loam extrudable mix is the visual physical appearance of the pre-pelleted feed, the chemical characteristic of the feed is a function of the solvent and solute relationship, thus each "mix" has unique performance characteristics.

Whereas in typical pelleting operations liquids are added to the mix in the form of lubricating agents or binders, in the present method liquids, i.e. solvents, are added to modify the ORTHENE® technical in order to form an improved "plastic" range of the extrusion mixture. Thus, given the solubility of the insecticide in a set of solvents (which can readily be determined by known methods) and the proper amount of solvent to be used for one of the solvents (which is readily determined by testing pellet properties over a range of solvent:insecticide ratios), as a first order estimate for the proper amount of a second solvent, if the insecticide is less soluble in the second solvent, then more of the second solvent will be required to attain the proper extrudate consistency and pellet properties. The mixture is extruded through an extruder having appropriately-sized orifices, conveniently under an L/d extrusion performance ratio of about 8. The L/d performance ratio is a well known term in the extrusion art and relates the effective thickness of a die to the diameter of a pellet attained.

The heat caused from the pressure of extrusion will contemporaneously evaporate a substantial portion of the solvent from the extrusion product as it is formed, which is an advantage of the present invention. Any residual solvent can be removed by vacuum and/or air drying the extruded product, or by application of direct or indirect heat, if necessary. As the extrusion product exits the extruding orifice, the product is cut to appropriate size, usually about 3 mm to 10 mm in length.

According to an alternative method, the dry ingredients including the insecticidal compound may be mixed with a suitable solvent to form a flowable mixture, which may be, but need not necessarily be, a solution. The flowable mixture is then placed into a mold or other container and the solvent is evaporated to form a solid molded form. The solid molded form is then released from the mold. Since the flowable mixture is not extruded, the amount of solvent is not particularly critical and the dry ingredients-to-solvent ratio to form the flowable mixture may be, for example, in the range of about 5–80% by weight of solvent. The mold may be in the form of, for example, bricks or stakes to form a solid insecticidal composition. The molds may also be in the form of pills, pellets or tablets so that when released from the mold the composition is already in a pelletized form. Alternatively, the composition may be molded as a solid form, such as a brick, and then divided into fragments, such as by cutting or impact fragmentation and sieved to the desired size.

In another alternative, the insecticidal compound (with or without the additives) in technical form may be melted (ORTHENE® melts at about 90° C.) and the melt may be placed in a mold to form bricks, tablets, pellets, and the like. Optionally, the bricks may be again divided into fragments by cutting or fragmentation, etc.

In yet another alternative, the melt of insecticidal compound may be passed through an orifice to form pellet-sized drops and then the drops will be solidified. In the usual instance, the drops are solidified by dropping onto a cold surface, i.e., a surface which is at a temperature lower than the temperature of the drops.

In each of the above cases, a polymeric surfactant may be added in the amount of about 20% or less, by weight, to assist in the dispersion of the formulation on crops.

It will be readily apparent to those of ordinary skill in the art that other methods of making pellets may be utilized given the foregoing disclosure. The pellets according to the present invention will have an attrition resistance of at least 92% as determined by ASTM method D4058-87 on 5 mm (length)× 2.38 mm (diam.) pellet. The mean hardness will also be greater than about 1.5 lb-F as determined by ASTM method D3313-88, and bulk density will be at least about 42 lb/ft$^3$ (about 0.68 gm/cc). These characteristics impart advantageous features, as discussed above, to the present invention as compared to powdered commercial ORTHENE® compositions. In general pellets of ORTHENE® made in accordance with the present invention will exhibit improved odor control over commercial powdered formulations, such as ORTHENE® 75S. Organothio odor is generally reduced by a factor at least 10 (ambient storage conditions) and thermal stability is improved over that of ORTHENE® 75S.

The following examples are provided by way of illustration and not intended to limit the invention in any way.

EXAMPLE 1

One hundred kg batches of technical ORTHENE® made at the Chevron Chemical facility in Richmond, Calif. were used to prepare pellets. The batches of technical ORTHENE® were mixed with 12% by weight of dichloromethane to a damp sandy loam consistency in a Nauta cone blender (Day Mixing Company, 5×3 ft.) and fed to a laboratory scale California pellet mill equipped with a 1.59 mm, 2.38 mm or 4.76 mm diameter pellet ss die, 12.7 cm ID. Most of the solvent evaporated from the extruded product as they exited the die. The residual solvent was removed by drying in a National vacuum oven (4.5 cubic feet).

Results are given below in Table 2 for various batches including batches using different extrusion die sizes, batches containing fragrances, ammonium sulfate, and/or magnesium sulfate.

TABLE 2

LIST OF ORTHENE ®
PELLETS PREPARED ON THE CALIFORNIA PELLET MILL

| Product Description (Made in the CA Pellet Mill) | Pellet Size Diameter | Sample Size | Hardness Lb-F (Mean) | Standard Deviation | Solubility 5 g/500 g Wtr |
|---|---|---|---|---|---|
| 1. ORTHENE ® tech 99% pellets | 4.76 mm | 1.5 kg | 3.81 | 1.31 | 3'40" |
| 2. ORTHENE ® tech 2% $MgSO_4$ 0.5% Alpine | 4.76 mm | 1.5 kg | 3.21 | 0.74 | 3'30" |
| 3. ORTHENE ® tech, 2% Ammonium sulfate | 4.76 mm | 1.5 kg | 4.59 | 0.92 | 3'32" |
| 4. ORTHENE ® tech, Mfg. (2 min. spin) | 4.76 mm | 1.5 kg | 6.06 | 2.38 | 4'41" |
| 5. ORTHENE ® tech, Alpine 0.5% | 4.76 mm | 1.5 kg | 1.98 | 0.43 | — |
| 6. ORTHENE ® 99% tech | 4.76 mm | 1.5 kg | 3.25 | 1.5 | — |
| 7. ORTHENE ® tech, Ammonium sulfate 2% Alpine 0.5% | 4.76 mm | 1.5 kg | 3.74 | 0.71 | — |
| 8. ORTHENE ® tech 99% | 2.38 mm | 1.5 kg | 2.04 | 0.43 | 2'06" |
| 9. ORTHENE ® tech, Alpine 0.5% | 2.38 mm | 1.5 kg | 2.37 | 0.54 | — |
| 10. ORTHENEO tech 2% $MgSO_4$ 0.5% Alpine | 2.38 mm | 1.5 kg | 2.95 | 1.36 | 2'22" |
| 11. ORTHENE ® tech 99% | 1.59 mm | 1.5 kg | 1.72 | 0.41 | 1'48" |
| 12. ORTHENE ® tech, Ammonium sulfate | 1.59 mm | 1.5 kg | 2.59 | 0.76 | 1'31" |
| 13. ORTHENE ® tech, Magnesium sulfate | 1.59 mm | 3.0 kg | — | — | — |
| 14. ORTHENE ® tech, Ammonium sulfate | 1.59 mm | 3.0 kg | — | — | — |

EXAMPLE 2

Using the procedure of EXAMPLE 1 a batch of pellets was made using a mixture of total weight of 3178 grams comprising 10% by weight methylene chloride as a standard. Then pellets were made with ORTHENE® tech containing methylene chloride (10% by weight of the total sample) in 3178 grams of total composition including 95 grams of Pluronic F-108 (a surfactant). A third sample was made utilizing 467 grams of methylene chloride in 2.63 kg of ORTHENE® tech. All samples of pellets resulted in attrition resistance, bulk density and physical characteristics meeting the parameters of the present invention.

EXAMPLE 3

Pellets were made from tech ORTHENE® using different solvents. Different samples were used using 3–25% of each of the following solvents: chloroform, carbon tetrachloride, dichloroethane, deionized water, toluene, methanol, ethanol and isopropanol. Except in the case of toluene, carbon tetrachloride, isopropanol and dichloroethane, pellets were formed with sufficient physical properties to meet the parameters of the present invention. When using the alcohols and water, the initial extruded product was slightly wetter than when using the chlorinated solvents, however, the pellets could be dried to remove the moisture. Solubilities are given below for common solvents.

TABLE 3

Solubility of ORTHENE ® in Various Solvents

| Solvent | Grams ORTHENE ®/ 100 ml Solution |
|---|---|
| Water | 70 |

TABLE 3-continued

Solubility of ORTHENE ® in Various Solvents

| Solvent | Grams ORTHENE ®/ 100 ml Solution |
|---|---|
| Acetic Acid | ~65 |
| Pyrrole | ~62 |
| Chloroform | ~60 |
| 1,1,2,2-Tetrachloroethane | ~60 |
| Methyl Alcohol | ~55 |
| Dimethyl Sulfoxide | ~55 |
| Dimethylformamide | ~54 |
| Methylene Chloride | 51 |
| N-Methylpyrrolidone | ~50 |
| Acetonitrile | ~44 |
| Methyl Cellosolve | ~40 |
| Ethylene Glycol | ~38 |
| Ethyl Alcohol | 34 |
| Tetrahydrofurfuryl Alcohol | ~32 |
| Carbitol | ~30 |
| Cellosolve | ~28 |
| Methyl Carbitol | ~26 |
| Ethylene Dichloride | ~25 |
| Diacetone Alcohol | ~23 |
| Propylene Glycol Monomethyl Ether | ~22 |
| Propylene Glycol | ~20 |
| Acetone | 15 |
| n-Butyl Alcohol | ~15 |
| Isopropyl Alcohol | ~15 |
| Methyl Ethyl Ketone | ~14 |
| Tributyl Phosphate | <15 |
| Triethyl Phosphate | <15 |
| Amyl Alcohol | ~12 |
| Butyl Cellosolve | ~10 |
| Dioxane | ~10 |
| Dipropylene Glycol | ~10 |
| Tripropylene Glycol Monomethyl Ether | ~10 |
| Dimethyl Carbitol | <10 |
| Carbitol Acetate | <10 |

TABLE 3-continued

Solubility of ORTHENE ® in Various Solvents

| Solvent | Grams ORTHENE ®/ 100 ml Solution |
|---|---|
| Ethylene Glycol Diacetate | <10 |
| Methyl Cellosolve Acetate | <10 |
| Perchloroethylene | <10 |
| n-Hexyl Alcohol | ~9 |
| n-Amyl Alcohol | ~5 |
| Isophorone | ~5 |
| Carbon Tetrachloride | <5 |
| Cyclohexanone | <5 |
| Glycerol Triacetate | <5 |
| Pine Oil | <5 |
| Methyl Isobutyl Ketone | ~4 |
| Ethyl Acetate | 3.47 |
| n-Octyl Alcohol | ~3 |
| Pentoxone | ~3 |
| 1,1,1-Trichloroethane | 2 |
| Perchloroethylene | 2 |
| Benzene | 1.57 |
| Toluene | 0.68 |
| Ether | 0.61 |
| Hexane | 0.01 |

NOTE: Neither ORTHENE ® 85 Technical nor ORTHENE ® 75 S can be dissolved to give a clear solution. While the ORTHENE ® does dissolve, the fine silica present does not. It will suspend in the solvent giving a cloudy appearance and some thickening of the solution.

EXAMPLE 4

To 3178 grams of ORTHENE® technical powder was added 220.21 gm deionized water. The resulting pellets were mushy in consistency and extruded poorly. To a balance of 3178 grams of water/ORTHENE® was added another 1362 grams dry ORTHENE® powder. The resulting extrusion was still poor. To 8898.4 gm dry ORTHENE® was added 363.2 grams of deionized water. The resulting extrusion met the requirements of the present invention.

What is claimed is:

1. A method for preparing pellets comprising a compound or mixture of compounds of the formula:

$$\begin{array}{c} \text{O} \quad\quad \text{O} \\ \text{R—Y} \quad \parallel \\ \diagdown \quad \text{C—R}^2 \\ \text{P—N} \\ \diagup \quad \diagdown \\ \text{R}^1\text{—S} \quad\quad \text{R}^3 \end{array}$$

where R and $R^1$ individually are alkyl, alkenyl or alkynyl of up to 6 carbon atoms, $R^3$ is hydrogen or alkyl of 1–6 carbon atoms, $R^2$ is hydrogen, alkyl of 1–18 carbon atoms, cycloalkyl of 3–8 carbon atoms, alkenyl of 2–18 carbon atoms or alkynyl of 3–18 carbon atoms, and Y is oxygen or sulfur; comprising the steps of (a) forming an extrudable mixture comprising said compound in from 3–25% by weight of a solvent, said solvent characterized as having a solubility of said compound therein of at least about 0.5 gm/100 ml;

(b) forming said pellets by extrusion.

2. A method according to claim 1 wherein said mixture further comprises a surfactant.

3. A method according to claim 1 further comprising the step (c) of applying an anti-caking agent to said pellets.

4. A method according to claim 1 wherein said mixture further comprises ammonium sulfate.

5. A method according to claim 1 wherein said mixture further comprises substantially anhydrous magnesium sulfate.

6. A method according to claim 1 wherein said solvent comprises methylene chloride.

7. A method according to claim 1 wherein R and $R^1$ are independently methyl, ethyl, allyl or alkenyl; $R^2$ is H or alkyl; $R^3$ is hydrogen and Y is oxygen.

8. A method according to claim 7 wherein R, $R^1$, and $R^2$ are methyl; $R^3$ is hydrogen.

9. A method for preparing a solid insecticidal composition comprising a compound or mixture of compounds of the formula:

$$\begin{array}{c} \text{O} \quad\quad \text{O} \\ \text{R—Y} \quad \parallel \\ \diagdown \quad \text{C—R}^2 \\ \text{P—N} \\ \diagup \quad \diagdown \\ \text{R}^1\text{—S} \quad\quad \text{R}^3 \end{array}$$

where R and $R^1$ individually are alkyl, alkenyl or alkynyl of up to 6 carbon atoms, $R^3$ is hydrogen or alkyl of 1–6 carbon atoms, $R^2$ is hydrogen, alkyl of 1–18 carbon atoms, cycloalkyl of 3–8 carbon atoms, alkenyl of 2–18 carbon atoms or alkynyl of 3–18 carbon atoms, and Y is oxygen or sulfur comprising the steps of:

(a) forming a flowable mixture or solution comprising said compound and a solvent in which said compound is soluble to the extent of at least about 0.5 gm/100 ml;

(b) placing said mixture into molding means;

(c) evaporating said solvent to form a solid molded form; and (d) releasing said molded form from said molding means.

10. A method according to claim 9 wherein said mixture comprises a surfactant.

11. A method according to claim 9 wherein said mixture comprises an anti-caking agent.

12. A method according to claim 9 wherein said mixture comprises ammonium sulfate.

13. A method according to claim 9 wherein said mixture comprises essentially anhydrous magnesium sulfate.

14. A method according to claim 9 wherein in said step (a) said mixture comprises a solution.

15. A method according to claim 9 wherein in said step (a) said mixture comprises a flowable dough-like texture.

16. A method according to claim 9 wherein said solvent comprises methylene chloride.

17. A method according to claim 9 wherein R and $R^1$ are independently methyl, ethyl, allyl or alkenyl; $R^2$ is H or alkyl; $R^3$ is hydrogen and Y is oxygen.

18. A method according to claim 17 wherein R, $R^1$, and $R^2$ are methyl; $R^3$ is hydrogen.

19. A method according to claim 9 further comprising the step of fragmenting said molded form by impact fragmentation.

20. A method according to claim 9 further comprising the step of fragmenting said molded form by cutting.

21. A method for preparing a solid insecticidal composition comprising a compound or a mixture of compounds of the formula:

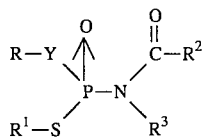

where R and R$^1$ individually are alkyl, alkenyl or alkynyl of up to 6 carbon atoms, R$^3$ is hydrogen or alkyl of 1–6 carbon atoms, R$^2$ is hydrogen, alkyl of 1–18 carbon atoms, cycloalkyl of 3–8 carbon atoms, alkenyl of 2–18 carbon atoms or alkynyl of 3–18 carbon atoms, and Y is oxygen or sulfur comprising the steps of:

(a) contacting said compound in molten form into molding means;

(b) solidifying said molten form to produce a solid molded form; and (c) releasing said solid molded form from said molding means.

22. A method according to claim 21 wherein said molten form further comprises a surfactant.

23. A method according to claim 21 wherein said molten form further comprises an anti-caking agent.

24. A method according to claim 21 wherein said molten form further comprises ammonium sulfate.

25. A method according to claim 21 wherein said molten form further comprises essentially anhydrous magnesium sulfate.

26. A method according to claim 21 wherein R and R$^1$ are independently methyl, ethyl, allyl or alkenyl; R$^2$ is H or alkyl; R$^3$ is hydrogen and Y is oxygen.

27. A method according to claim 26 wherein R, R$^1$, and R$^2$ are methyl; R$^3$ is hydrogen.

28. A method according to claim 21 further comprising the step of fragmenting said molded form by impact fragmentation.

29. A method according to claim 21 further comprising the step of fragmenting said molded form by cutting.

30. A method for preparing pellets comprising a compound or mixture of compounds of the formula:

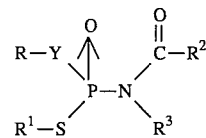

where R and R$^1$ individually are alkyl, alkenyl or alkynyl of up to 6 carbon atoms, R$^3$ is hydrogen or alkyl of 1–6 carbon atoms, R$^2$ is hydrogen, alkyl of 1–18 carbon atoms, cycloalkyl of 3–8 carbon atoms, alkenyl of 2–18 carbon atoms or alkynyl of 3–18 carbon atoms, and Y is oxygen or sulfur comprising the steps of:

(a) passing said compound in molten form through an orifice to form molten pellet-sized drops of said compound, and (b) solidifying said drops.

31. A method according to claim 30 wherein said step (b) comprises contacting said drops with a surface, said surface being at a temperature lower than the temperature of said drops.

32. A method according to claim 30 wherein said molten form further comprises a surfactant.

33. A method according to claim 30 wherein said molten form further comprises an anti-caking agent.

34. A method according to claim 30 wherein said molten form further comprises ammonium sulfate.

35. A method according to claim 30 wherein said molten form further comprises essentially anhydrous magnesium sulfate.

36. A method according to claim 30 wherein R and R$^1$ are independently methyl, ethyl, allyl or alkenyl; R$^2$ is H or alkyl; R$^3$ is hydrogen and Y is oxygen.

37. A method according to claim 30 wherein R, R$^1$, and R$^2$ are methyl; and R$^3$ is hydrogen.

38. A method according to any one of claims 2, 10, 22 or 32 wherein said surfactant comprises a polymeric surfactant.

39. A method according to any one of claims 3, 11, 23 or 33 wherein said anti-caking agent comprises fumed silica.

* * * * *